United States Patent [19]

Dufek

[11] 4,021,462
[45] May 3, 1977

[54] ISOLATION OF CARBOXY-SUBSTITUTED ALIPHATIC HYDROCARBONS

[75] Inventor: Edward J. Dufek, Peoria, Ill.

[73] Assignee: The United States of America as represented by the Secretary of Agriculture, Washington, D.C.

[22] Filed: July 28, 1975

[21] Appl. No.: 599,497

[52] U.S. Cl. ............................... 260/419; 260/705
[51] Int. Cl.$^2$ ...................... C11C 1/00; C11C 1/08
[58] Field of Search ....... 260/418, 419, 412, 412.8, 260/410.9 R, 426, 705, 413

[56] References Cited

UNITED STATES PATENTS

| | | | |
|---|---|---|---|
| 2,895,976 | 7/1959 | Kairys et al. | 260/419 |
| 3,151,139 | 9/1964 | Van Der Plas | 260/419 |
| 3,917,660 | 11/1975 | Sasaki et al. | 260/404 |
| 3,928,231 | 12/1975 | Frankel | 260/410.9 R |

FOREIGN PATENTS OR APPLICATIONS 205,830   2/1968   U.S.S.R. ............................ 260/419

*Primary Examiner*—Helen M. McCarthy
*Attorney, Agent, or Firm*—M. Howard Silverstein; David G. McConnell; Curtis P. Ribando

[57] ABSTRACT

Carboxy-substituted aliphatic hydrocarbons in admixture are separated one from the other at up to about 95% purity by serial extraction into aqueous alkali.

10 Claims, No Drawings

ISOLATION OF CARBOXY-SUBSTITUTED ALIPHATIC HYDROCARBONS

BACKGROUND OF THE INVENTION

This invention relates to the isolation of carboxy-substituted aliphatic hydrocarbons predominantly free from carboxy-substituted aliphatic hydrocarbons having different degrees of carboxy substitution.

Specifically, the invention relates to the isolation, one from the other, of mono-, di-, and tricarboxy-substituted fatty alkyl esters which occur in mixtures with the unsubstituted fatty alkyl esters and other neutral compounds.

The foregoing mixtures may be conventionally obtained by hydroformylation and the oxidation of unsaturated fatty alkyl esters. The unsaturated fatty alkyl esters are obtained by methods well known in the art from vegetable oils such as olive, soybean, safflower, and linseed oil. Vegetable oils are normally mixtures of various unsaturated aliphatic glycerides. Each aliphatic chain can be either mono-, di-, or triunsaturated. For example, the triunsaturated alkyl fatty ester methyl linoleate is found predominantly in transesterified linseed oil.

The unsaturated fatty alkyl esters are first hydroformylated, preferably by the method of Frankel disclosed in U.S. Pat. No. 3,787,459. This method is desirable because it yields products exhibiting little or no isomerization. In this hydroformylation process unsaturated bonds are reacted with hydrogen and carbon monoxide in the presence of a rhodium metal-trisubstituted phosphine catalyst admixture. The resulting product, depending upon the starting material, contains formyl substituents on either, but not both, carbon atoms found at each end of every double bond in the unsaturated fatty alkyl ester.

The formyl groups are then oxidized by the permanganate method disclosed in Frankel, supra, by dichromate (Dufek et al., J. Amer. Oil Chem. Soc. 49: 302–306 [1972]), or by catalytic reaction with gaseous oxygen (Schwab, U.S. Pat. No. 3,804,895). The formyl substituents are converted to carboxy groups, thus yielding a mixture of acidic fatty alkyl esters with a carboxy group attached to one of the carbons at each of the original sites of unsaturation in the fatty alkyl ester. For example, hydroformylation and oxidation of soybean oil methyl esters yields the following three stearates:

These mixtures of carboxy-substituted fatty alkyl esters are useful for the same purposes as fatty acids. The carboxy groups then may be esterified by conventional methods (Dufek et al., supra) to yield polyesters valuable as intermediates in the preparation of polyamides used in leather finishing (U.S. Pat. No. 2,957,783); in adhesives, castings, and protective coatings (U.S. Pat. No. 3,062,273), in plasticizing vinyl halide resins (U.S. Pat. No. 2,965,598), and as lubricants (Dufek et al., supra).

The use of these polyester mixtures as high temperature lubricants has been handicapped by the presence of low boiling components. The greater the ester substitution of the aliphatic hydrocarbon the higher the boiling point, so it is highly desirable to provide the most highly substituted hydrocarbon as the principal lubricant component. This can be accomplished by separating the highly substituted compounds before esterification.

Therefore, it is an object of this invention to procure isolates of mono- and polycarboxy-substituted aliphatic hydrocarbons in high yields and at high levels of purity.

It is a further object of this invention to procure these isolates from complex mixtures of such hydrocarbons in a simple and expedient fashion.

I have discovered a process for separating a carboxy-substituted aliphatic hydrocarbon mixture into fractions, each fraction having as its predominant component a carboxy-substituted aliphatic hydrocarbon exhibiting a single degree of carboxy substitution, the process comprising serially extracting a solution of the mixture with aliquots of aqueous alkali, separating each aliquot from the solution, acidifying each aliquot, and recovering the desired carboxy-substituted aliphatic hydrocarbon fraction. By the process of the instant invention the most highly carboxy-substituted aliphatic hydrocarbons are extracted first, followed by components having a lesser degree of carboxy substitution until only neutral hydrocarbons remain. This result was entirely unexpected because those skilled in the art would expect alkali to react without any preference with any acidic component of similar structure, thus extracting all acid components in the same proportion that they occur in the starting mixture.

DETAILED DESCRIPTION OF THE INVENTION

The carboxy-substituted aliphatic hydrocarbon mixtures which may be separated by the process of this invention are those comprising $C_{12}$ to $C_{22}$ normal aliphatic hydrocarbons which have been substituted with carboxy groups, either internally or at the carbon chain termini; the carboxy groups are each covalently bonded to the aliphatic hydrocarbon backbone. The

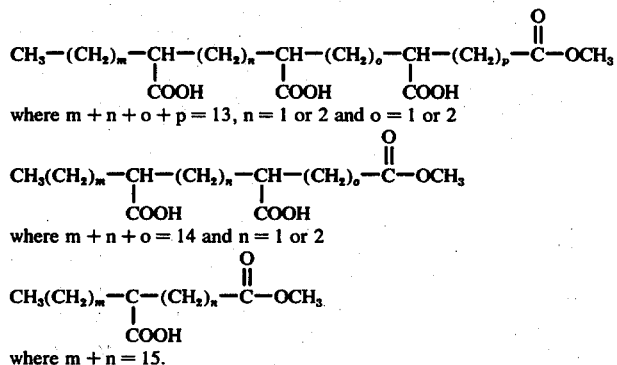

(I) $CH_3-(CH_2)_m-\underset{COOH}{CH}-(CH_2)_n-\underset{COOH}{CH}-(CH_2)_o-\underset{COOH}{CH}-(CH_2)_p-\overset{O}{\underset{\|}{C}}-OCH_3$ where $m + n + o + p = 13$, $n = 1$ or $2$ and $o = 1$ or $2$ (II) $CH_3(CH_2)_m-\underset{COOH}{CH}-(CH_2)_n-\underset{COOH}{CH}-(CH_2)_o-\overset{O}{\underset{\|}{C}}-OCH_3$ where $m + n + o = 14$ and $n = 1$ or $2$ (III) $CH_3(CH_2)_m-\underset{COOH}{C}-(CH_2)_n-\overset{O}{\underset{\|}{C}}-OCH_3$ where $m + n = 15$.

Of course, the presence of di-, tri-, or higher carboxy-substituted fatty alkyl esters and the predominance of each ester will depend upon the unsaturation of the starting material.

inventive process contemplates that the mixtures contain at least two carboxy-substituted hydrocarbons having different degrees of carboxy substitution, for example a preponderance of ethyl monocarboxy palmitate and a minor amount of methyl dicarboxy palmitate. Mixtures comprising tricarboxy and higher polycarboxy compounds may also be fractionated by the inventive process. The substituted hydrocarbons may be saturated or unsaturated, and may be additionally substituted with lower alkyl esters. Degree of carboxy substitution is defined herein to include only carboxy groups and not lower alkyl ester groups. The mixtures obtained by the hydroformylation and oxidation of unsaturated fatty alkyl esters are convenient starting mixtures although the particular method for production of these mixtures is immaterial. Such mixtures generally comprise lower alkyl esters of mono-, di-, and tricarboxy stearate (i.e., lower alkyl esters wherein degrees of carboxy substitution is by 1, 2, and 3 carboxy groups, respectively). A lower alkyl carboxy stearate is one in which the stearic acid terminal carboxy is esterified with a lower alkyl group, i.e., $C_2$ to $C_5$. The mixtures herein described are dissolved in a suitable solvent readily determinable by the skilled artisan. For example, ether, hexane, pentane, or petroleum ether are satisfactory. Ether is preferred because its high volatility permits rapid drying.

Alkali is intended to encompass the alkali metal and ammonium hydroxides and carbonates. The preferred alkali metals are sodium or potassium, for economic reasons, and bicarbonate is preferred for its greater selectivity with respect to polycarboxy compounds as opposed to monocarboxy species. This latter point is discussed infra. The alkali is employed in aqueous solution when extracting the mixture solution, and its concentration is not critical. Lower alkyl alcohols may be optionally added to the aqueous alkali to ensure that the extracted ammonium and alkali metal carboxy and polycarboxy salts remain soluble.

The purity of a particular carboxy-substituted aliphatic hydrocarbon in each recovered extract will in general depend upon control of the amount of alkali in the extraction aliquot. This control may be accomplished by increasing the number of aliquots while reducing the alkali content of each, followed by analyzing each recovered extract and combining the extracts containing the greatest proportions of the desired component. This is essentially a trial and error procedure. Alternatively, the mixture may be analyzed, for example, by gas-liquid chromatography (GLC), to determine the quantity of each carboxy-substituted aliphatic hydrocarbon component, the stoichiometric amount of alkali needed to neutralize the most highly substituted component calculated and the mixture solution extracted with one or more aliquots of alkali which in sum contain an approximately 5% to 10% excess of alkali over the calculated stoichiometric amount. The same sequence of steps is repeated for each successive component, hence the mixture solution is serially extracted.

Unexpectedly, when using an alkali metal bicarbonate in the inventive process it is unnecessary to control the amount of bicarbonate when extracting dicarboxy- and other polycarboxy-substituted aliphatic hydrocarbons from a mixture also containing the monocarboxy-substituted species. Large, excessive amounts of bicarbonate may be employed, yet no significant monocarboxy species is extracted. Like other alkalis, however, control of the amount of bicarbonate is desirable when fractionating the polycarboxy species.

In practicing the instant invention the mixture solution and aqueous alkali are thoroughly admixed to enhance extraction and, after a period of time sufficient for the alkali to react with the carboxy groups and for the aqueous alkali to solubilize the neutralized carboxy groups, the aqueous layer is separated. If the amount of alkali needed to neutralize and extract a given carboxy-substituted component has been calculated, that alkali aliquot may be employed in a single extraction or subdivided into aliquots for fractional extractions which are later combined. The latter procedure is more effective in obtaining high yields and purity but is of course less economical than a single extraction. Similarly, re-extracting the aqueous alkali extract before acidification with portions of the solvent used for the mixture will reduce minor contamination by mixture droplets suspended in the aqueous alkali extracts, but an extra extraction step is thus required.

Following extraction each aqueous alkali aliquot is acidified, either before or after combination with other aliquots into fractions as desired. Only sufficient acid need be added to lower the pH below 7, and a suitable solvent for the acid carboxy-substituted hydrocarbon may be added to the aliquot to speed removal from the aqueous aliquot of the now essentially water-insoluble carboxy compound. The carboxy-substituted hydrocarbon may then be washed with water to remove residual impurities and the solvent stripped off if solvent was employed.

The following examples are intended only as illustrative embodiments and should not limit the scope of the invention.

A. Serial Extraction of Methyl Carboxystearates with NaOH

EXAMPLE 1

480 g. of oxidized-hydroformylated soybean oil methyl esters containing 6.9% methyl tricarboxystearate, 43.6% methyl dicarboxystearate, 29.4% methyl carboxystearate (including 4.4% methyl formoxystearate), 6.0% methyl stearate, and 11.1% methyl palmitate were dissolved in ether and serially extracted with six aliquots of 5% aqueous-methanolic NaOH or aqueous NaOH as further described in Table 1. Each aliquot was acidified, thus producing an oily layer which was recovered and analyzed by GLC to determine the content of methyl palmitate, methyl stearate, methyl carboxystearate, methyl dicarboxystearate, and methyl tricarboxystearate. The yield and neutral equivalent for each layer was also determined. The serially extracted ether was washed with water and evaporated to predominantly yield neutral fatty acid esters. All results are set forth in Table 1.

EXAMPLE 2

996 g. of oxidized-hydroformylated safflower oil methyl esters were dissolved in 300 ml. of ether. The ether solution, analyzed by GLC, contained 69.4% methyl dicarboxystearate, 17.2% methyl monocarboxystearate, 3.1% methyl stearate, 7.8% methyl palmitate, and small amounts of short chain products.

The ether solution was extracted with six aliquots of 5% aqueous NaOH as further described in Table 1. Each aliquot was acidified and the oily layer assayed to the extent set forth in Table 1. Aliquots 1, 2, and 3 were combined to give 553.4 g. of methyl dicarboxystearate; neutral equivalent 203, calc. 193.

B. Serial Extraction of Methyl Carboxystearates with Bicarbonate and NaOH

EXAMPLE 3

480 g. of oxidized-hydroformylated soybean oil methyl esters were dissolved in ether and serially extracted with five aliquots of 10% aqueous or aqueous-methanolic alkali metal bicarbonate as further described in Table 1. Each aliquot was acidified, thus producing an oily layer which was recovered and analyzed by GLC to determine the content of methyl palmitate, methyl stearate, methyl carboxystearate, methyl dicarboxystearate, and methyl tricarboxystearate. The yield and neutral equivalent for each layer was also determined. The bicarbonate-extracted ether was then mixed with 5% aqueous NaOH, the pH raised to pH 11.8, and the aqueous NaOH separated from the ether and acidified, thus producing an oily layer which was recovered and analyzed as above. The ether was washed with water and evaporated to predominantly yield neutral fatty acid esters.

aqueous NaOH to a pH of 10 and the layers separated. The ether layer was then titrated to a pH of 11, separated and further titrated to a pH of 12. The NaOH solutions were all combined, extracted twice with ether, the ether separated, and the NaOH solution acidified, whereupon an oily layer formed which contained 58.3 g. of methyl monocarboxystearate and exhibited a neutral equivalent of 344.2, calc. 342.5.

All of the ether fractions were combined, washed with water and stripped to dryness to give 63.8 g. of neutral products.

Ether was then added to the combined $KHCO_3$ aliquots and the mixture acidified with HCl. The ether layer was then recovered, washed with water and stripped to dryness in vacuuo. The yield of methyl dicarboxystearate was 250.0 g. with a neutral equivalent of 200.9, calc. 193.7. The product was analyzed by GLC to contain 95.1% methyl dicarboxystearate with the remainder being mainly methyl monocarboxystearate.

EXAMPLE 5

833 g. of oxidized-hydroformylated linseed oil

Table 1

| Aliquot | Reagent | Yield pH | Yield g. | N.E.[b] | P[b] | S[b] | MeCS[b] | MeDiCS[b] | MeTriCS[b] |
|---|---|---|---|---|---|---|---|---|---|
| | | | | Example 1 | | | | | |
| 1 | ml. 5% NaOH 300 | 7.2 | 21.0 | 154.9 | Tr | 0.3 | Tr | 16.7 | 81.4 |
| 2 | 300 + 80 ml. MeOH | 7.6 | 117.8 | 203.1 | 0.6 | 0.6 | 3.1 | 88.0 | 7.7 |
| 3 | 300 | 8.9 | 110.5 | 241.3 | 1.2 | 2.6 | 14.3 | 79.5 | —[i] |
| 4 | 50 | 9.7 | 24.8 | 344.6 | 2.2 | 4.3 | 62.7 | 30.8 | — |
| 5 | 50 | 10.0 | 11.7 | 352.6 | 0.7 | 2.2 | 74.3 | 21.3 | — |
| 6 | 200 | 12.8 | 90.5 | 280.9 | 0.2 | 0.4 | 87.3 | 11.8 | — |
| | Neutrals | | 94.8 | 2.1%[d] | 54.0 | 24.4 | 26.3[e] | 11.5[f] | — |
| | Total | | 471.1 | | | | | | |
| | | | | Example 2 | | | | | |
| 1 | ml. 5% NaOH 800 | — | 35.8 | — | — | — | 1.3 | 95.0 | — |
| 2 | 800 | — | 403.5 | — | — | — | 2.8 | 92.7 | — |
| 3 | 400 | — | 114.1 | — | — | — | 2.1 | 94.8 | — |
| 4 | 300 | — | 96.1 | — | — | — | 19.7 | 62.5 | — |
| 5 | 800 | — | 212.6 | — | — | — | 57.5 | 27.5 | — |
| 6 | 800 | — | 3.4 | — | — | — | — | — | — |
| | Neutrals | | 195.2 | | | | | | |
| | Total | | 1060.7 | | | | | | |
| | | | | Example 3 | | | | | |
| 1 | ml. 10% $NaHCO_3$ 250 | 7.3 | 17.2 | 150.2 | Tr | 0.3 | 0.5 | 7.5 | 87.8 |
| 2 | 250 + 80 ml. MeOH | 7.6 | 42.1 | 193.5 | Tr | Tr | 1.0 | 80.0 | 15.8 |
| 3 | 250 + 80 ml. MeOH | 7.9 | 41.7 | 199.8 | Tr | Tr | 1.4 | 90.0 | 7.2 |
| 4 | 250 + 80 ml. MeOH | — | 87.9 | 210.9 | 0.7 | 0.8 | 4.7 | 93.5 | — |
| 5 | 250 + 80 ml. MeOH | 8.4 | 22.5 | 208.7 | 0.4 | 0.4 | 2.2 | 92.6 | — |
| 6 | Add 5% NaOH to pH | 11.8 | 137.4 | 355.0 | 2.3 | 3.4 | 65.5 | 27.0[g] | — |
| | Neutrals[h] | | 126.9 | 19.2%[d] | 23.2 | 19.2 | 20.3 | 13.2[f] | — |
| | Total | | 475.7 | | | | | | |

[a]Plus short chain and trace amounts of unidentified products to total 100%.
[b]N.E. = neutral equivalent, P = methyl palmitate, S = methyl stearate, MeCS = methyl carboxystearate, MeDiCS = methyl dicarboxystearate, MeTriCS = methyl tricarboxystearate.
[c]Calculated as MeCS.
[d]Includes 23.0% methyl formyl- and/or formoxystearate.
[e]Unidentified disubstituted products such as methyl bis-formoxystearate.
[f]May contain methyl formoxycarboxystearate.
[h]Also contains 18.4% methyl hydroxy-, keto- and formoxystearate.
[i]Indicates assay was not done.

EXAMPLE 4

An ether solution of oxidized-hydroformylated safflower oil methyl esters was extracted five times with 250-ml. aliquots of 10% aqueous $KHCO_3$. The aliquots were combined and washed twice with ether. The ether washes were combined with the extracted ether solution, the combined solution titrated with cold 50% methyl esters were dissolved in ether and extracted with five 250-ml. aliquots of a solution containing 25 g. $NaHCO_3$, 150 ml. of water, and 100 ml. of methanol. The aliquots were combined and washed twice with ether. The ether washings and the extracted ether were combined and extracted further with three 300-ml. aliquots of solution containing 50 g. $NaHCO_3$ in 300 ml. of water. These three aliquots were combined and washed twice with ether. The ether washings and the extracted ether were combined and titrated with cold 50% aqueous NaOH as in Example 4. The NaOH layers were mixed with ether and acidified. The acidified ether layer thereby produced was washed with water, stripped to dryness and assayed to yield 212.9 g. of methyl monocarboxystearates with a neutral equivalent of 335.2, calc. 342.5.

The remaining ether solutions were combined, washed with water and stripped to dryness, thus yielding 96.3 g. of neutral products, e.g., methyl palmitate and methyl stearate.

Ether was added to the combined four NaHCO₃ extracts and the mixture acidified with HCl. The ether layer was then washed with water and stripped to dryness, yielding 279.3 g. of a product having a neutral equivalent of 158.0, calc. 143.3, and containing by GLC analysis 91.5% methyl tricarboxystearate, 2.5% methyl dicarboxystearate, 2% methyl stearate and minor amounts of short chain methyl esters.

In a similar manner the combined three NaHCO₃ extracts were acidified with HCl, washed with water, stripped to dryness yielding 225.4 g. of a product having a neutral equivalent of 205.1, calculated for methyl dicarboxystearate, 193.

EXAMPLE 6

99 g. of oxidized-hydroformylated safflower oil butyl esters were dissolved in ether and extracted with two 150-ml. aliquots of a solution containing 25 g. NaHCO₃, 100 ml. of water and 50 ml. of methanol. The aliquots were combined and washed twice with ether. Ether was added to the aqueous NaHCO₃ extract and acidified with HCl. The ether layer was separated, washed with water and stripped to dryness to give 33.3 g. of butyl dicarboxystearate with a neutral equivalent of 227.0, calc. 214, and containing by GLC analysis 92.6% butyl dicarboxystearate and minor amounts of other shorter chain butyl esters.

I claim:

1. A process for separating carboxy-substituted aliphatic hydrocarbon mixtures into fractions, each fraction having as its predominant component a carboxy-substituted aliphatic hydrocarbon exhibiting a single degree of carboxy substitution, the process comprising the following steps:
    a. serially extracting a solution of said mixture with at least one aliquot of aqueous alkali metal bicarbonate, wherein the amount of alkali metal bicarbonate employed in said aliquot is at most an about 5% to 10% excess over the stoichiometric amount needed to neutralize the carboxy groups of the desired carboxy-substituted aliphatic hydrocarbon fraction;
    b. separating said at least one aliquot from said solution;
    c. acidifying said aliquot; and
    d. recovering said desired carboxy-substituted aliphatic hydrocarbon fraction.

2. The process of claim 1 wherein the solution of said mixture is extracted with at least two aliquots of aqueous alkali and including the additional step of combining said at least two aliquots after serial extraction but before acidification.

3. The process of claim 1 wherein the highest degree of carboxy substitution is by three carboxy groups.

4. The process of claim 1 wherein the mixture is in solution with ether.

5. A process for separating carboxy-substituted aliphatic hydrocarbon mixtures into fractions, wherein said mixture includes a monocarboxy-substituted aliphatic hydrocarbon, and wherein each fraction has as its predominant component a carboxy-substituted aliphatic hydrocarbon exhibiting a single degree of carboxy substitution, the process comprising the following steps:
    a. serially extracting a solution of said mixture with at least one aliquot of aqueous alkali metal bicarbonate;
    b. separating said at least one aliquot from said solution;
    c. acidifying said aliquot; and
    d. recovering said desired carboxy-substituted aliphatic hydrocarbon fraction.

6. The process of claim 5 wherein the solution of said mixture is extracted with at least two aliquots of aqueous alkali and including the additional step of combining said at least two aliquots after serial extraction but before acidification.

7. The process of claim 5 wherein the highest degree of carboxy substitution is by three carboxy groups.

8. The process of claim 5 wherein the mixture is in solution with ether.

9. The process of claim 5 wherein the amount of alkali employed in said at least one aliquot is at most an about 5% to 10% excess over the stoichiometric amount of alkali needed to neutralize the carboxy groups of the desired carboxy-substituted aliphatic hydrocarbon fraction.

10. A process for separating lower alkyl polycarboxystearate from lower alkyl monocarboxystearate, said process comprising serially extracting a solution of a mixture of both said lower alkyl polycarboxystearate and said lower alkyl monocarboxystearate with at least one aliquot of an aqueous solution of alkali metal bicarbonate wherein the amount of said bicarbonate in said at least one aliquot is in unknown excess of the stoichiometric amount of bicarbonate needed to neutralize the carboxy groups of said lower alkyl polycarboxystearate, separating said at least one aliquot from said solution, acidifying said aliquot and recovering the lower alkyl polycarboxystearate.

* * * * *